(12) United States Patent
Ben-Oren et al.

(10) Patent No.: US 8,622,920 B2
(45) Date of Patent: Jan. 7, 2014

(54) BREATH TEST DEVICE AND METHOD (75) Inventors: Ilan Ben-Oren, Modiin (IL); Avraham Hershkowitz, D.n. Shimshon (IL); Eli Kaplan, Ramat Hasharon (IL); Yaron Ilan, Jerusalem (IL)

(73) Assignee: Exalenz Bioscience Ltd., Modiin (IL)

( * ) Notice: Subject to any disclaimer, the term of this patent is extended or adjusted under 35 U.S.C. 154(b) by 312 days.

(21) Appl. No.: 12/084,629

(22) PCT Filed: Nov. 12, 2006

(86) PCT No.: PCT/IL2006/001296
§ 371 (c)(1),
(2), (4) Date: Sep. 16, 2009

(87) PCT Pub. No.: WO2007/054940
PCT Pub. Date: May 18, 2007

(65) Prior Publication Data
US 2010/0036273 A1    Feb. 11, 2010

Related U.S. Application Data

(60) Provisional application No. 60/735,479, filed on Nov. 11, 2005.

(51) Int. Cl.
*A61K 51/00*    (2006.01)
*A61B 5/097*    (2006.01)

(52) U.S. Cl.
USPC .......................................... 600/532; 600/529

(58) Field of Classification Search
USPC .................................. 600/529–543
See application file for complete search history.

(56) References Cited

U.S. PATENT DOCUMENTS 5,386,832 A * 2/1995 Wagner et al. ................. 600/532
5,486,699 A * 1/1996 Fabinski et al. ................ 250/345
(Continued)

FOREIGN PATENT DOCUMENTS

WO    99/12471    3/1999
WO    01/13091    3/2001

OTHER PUBLICATIONS

"13C-methacetin breath test as liver function test in patients with chronic hepatitis C virus infection" Braden et al. Alimentary Pharmacology & Therapeutics. 21 (2): 179-185. Jan. 2005.*
"13C-methacetin breath test for monitoring hepatic function in cirrhotic patients before and after liver transplantation" Petrolati et al. Alimentary Pharmacology & Therapeutics. 18 (8): 785-790. Oct. 2003.*
"Evaluation of the 13C-methacetin breath, test for quantitative liver function testing" Klatt et al. Z Gastroenterol. 35 (8): 609-14. Aug. 1997.*

(Continued)

*Primary Examiner* — Navin Natnithithadha
*Assistant Examiner* — Meredith Weare
(74) *Attorney, Agent, or Firm* — Rodney J. Fuller; Booth Udall Fuller, PLC (57) ABSTRACT

The disclosure relates to breath test devices and methods for the evaluation of liver functional and metabolic capacity or to assess liver heath and/or degree of liver injury. Specifically, there is provided a method of evaluating a liver condition, the method includes on-line monitoring a metabolic product of methacetin, a salt or a derivative of methacetin, in a subject's breath after administering to the subject isotope labeled methacetin, a salt or a derivative thereof in water solution form. There is also provided a device for evaluating a liver condition, the device includes one or more sensors adapted to monitor on-line an isotope level of a metabolic product of labeled methacetin, or a salt or a derivative of methacetin in a subject's breath and a controller adapted to sample measurements of the one or more sensors at a continuous mode.

25 Claims, 3 Drawing Sheets

(56) References Cited

U.S. PATENT DOCUMENTS

| | | | |
|---|---|---|---|
| 6,071,245 | A | 6/2000 | Kohno |
| 6,186,958 | B1* | 2/2001 | Katzman et al. ............... 600/532 |
| 6,491,643 | B2 | 12/2002 | Katzman et al. |
| 6,509,002 | B1 | 1/2003 | Kohno |
| 6,656,127 | B1 | 12/2003 | Ben-Oren et al. |
| RE38,728 | E | 4/2005 | Katzman et al. |
| 2001/0021815 | A1* | 9/2001 | Katzman et al. ............... 600/532 |
| 2003/0053049 | A1 | 3/2003 | Fink |
| 2003/0216660 | A1* | 11/2003 | Ben-Oren et al. ............ 600/532 |
| 2004/0122790 | A1 | 6/2004 | Walker |
| 2004/0152994 | A1* | 8/2004 | Meier-Augenstein ........ 600/532 |
| 2004/0253637 | A1 | 12/2004 | Buechler |
| 2005/0020931 | A1 | 1/2005 | Ben-Oren et al. |
| 2005/0177056 | A1* | 8/2005 | Giron et al. .................... 600/543 |
| 2007/0026480 | A1 | 2/2007 | Modak |
| 2007/0135725 | A1 | 6/2007 | Hatlestad |
| 2008/0167533 | A1 | 7/2008 | Leyendecker |
| 2009/0131810 | A1 | 5/2009 | Ben-Oren |
| 2010/0055734 | A1* | 3/2010 | Everson .......................... 435/29 |
| 2010/0143880 | A1* | 6/2010 | Stockmann et al. ............... 435/4 |
| 2010/0329979 | A1* | 12/2010 | Modak et al. ................ 424/1.81 |

OTHER PUBLICATIONS

Recent Materia Medica: Notes on their Origin and Therapeutics. Fourth Edition. Lescher, Frank Harwood. 1891.*
"N-(4-Methoxyphenyl)acetamide." http://www.chemicalbook.com/ChemicalProductProperty_EN_CB6310310.htm.*
"Automatic Quantification of Liver Fibrosis: Design and Validation of a New Image Analysis Method: Comparion with Semi-quantitative Indexes of Fibrosis." Masseroli et al. Journal of Hepatology 2000; 32: 453-464.*
"Dissolution Rate Studies III: Effect of Type and Intensity of Agitation on Dissolution Rate." Tingstad et al. Journal of Pharmaceutical Sciences. vol. 62, Issue 2, pp. 293-297, Feb. 1973.*
Festi et al. "Measurement of hepatic functional mass by means of 13C-methacetin and 13C-phenylalanine breath tests in chronic liver disease: Comparison with Child-Pugh score and serum bile acid levels." World J Gastroenterol. Jan. 7, 2005; 11(1):142-148.*
Giannini et al. "13C-Breath Tests and liver fibrosis." European Review for Medical and Pharmacological Sciences. 2004; 8: 51-54.*
Braden, et al, "13 C-methacetin breath test as liver function test in patients with chronic hepatitis C virus infection", Aliment Pharmacol Ther, 2005; 21, pp. 179-185.
Klatt, et al, "Evaluation of the 13 C-methacetin breath test for quantitative liver function testing", Z Gastroenterol. 1997; 35, pp. 609-614.
Candelli, Marcello et al., "13C-methacetin breath test: A new tool to predict the presence of liver vascular malformations in patients with hereditary haemorrhagic teleangiecstasia", AALSD p. 884A abstract #1446 (2007).
Everson, G. T. et al., "The spectrum of hepatic functional impairment in compensated chronic hepatitis C: results from the Hepatitis C Anti-viral Long-term Treatment against Cirrhosis Trial", Aliment Pharmacol Ther, 27(9):798-809 (2008).
Foufelle, Fabienne and Ferre, Pascal, "New perspectives in the regulation of hepatic glycolytic and lipogenic genes by insulin and glucose: a role for the transcription factor sterol regulatory element binding protein-1c", Biochem J, 366(pt 2):377-391 (2002).
Iwasaki, Ayami et al., "Study of liver function in babies with atopic dermatitis by using13C methacetin breath test", Allergy, Japan Office of Japanese Society of Allerology 41(6):645-653 (translated abstract) (1992).
Kleiner, David E. et al., "Design and validation of a histological scoring system for nonalcoholic fatty liver disease", Hepatology, 41(6):1313-1321 (2005).
Kumar, M. et al., "Histological subclassification of cirrhosis based on histological-haemodynamic correlation", Aliment Pharmacol Ther 27(9):771-779 (2008).
Petrolati, A. et al., "13C-methacetin breath test for monitoring hepatic function in cirrhotic patients before and after liver transplantation", Aliment Pharmacol Ther, 18:785-790 (2003).
Randle, P. J. et al., "The glucosefatty acid cycle: its role in insulin sensitivity and the metabolic disturbances in diabetes mellitus", Lancet, 281(7285):785-789 (1963).
ISR of PCT/IL2006/001296 mailed May 11, 2009.
ISR of PCT/IL09/00730 mailed Jan. 11, 2010.
EP 06809856 Supplementary European Search Report Mar. 15, 2011.
How Is Metabolic Syndrome Diagnosed? US Department of Health & Human Services. National Institute of Health. National Heart Lung and Blood Institute. Diseases and Conditions Index. Retrieved from http://nhlbi.nih.gov/health/doi/Diseases/ms diagnosis,html on Sep. 11, 2008.
Histological Scoring System for Nonalcoholic Fatty Liver Disease (NAFLD). Components of NAFLD Activity Score (NAS) and Fibrosis Staging. retrieved from http://www.medicalcriteria.com/criteria/gas nafld.htm on May 31, 2006.
Purified Water (PW) Edstrom Industries, Inc. retrieved from http://www.edstrom.com/Resources.cfm?doc id+174 on Sep. 11, 2008.
Citric Acid Cycle.Wikipedia.org retrieved from http://en.wikipedia.org/wiki/Citric_acid_cycle on Sep. 11, 2008.
Acetyl-CoA. Wikipedia.org retrieved from http://en.wikipedia.org/wiki/Acetyl-CoA on Sep. 11, 2008.
Multivariate analysis. Wikipedia.org retrieved from http://en.wikipedia.org/wiki/Multivariate analysis on Sep. 11, 2008.
Logistic regression. Wikipedia.org retrieved from http://en.wikipedia.org/wiki/Logistic regression on Sep. 11, 2008.
U.S. Appl. No. 12/219,824 Non-Final Rejection May 9, 2012.
Lalazar et al., (2009) Point-of-care continuous (13)C-methacetin breath test improves decision making in acute liver disease: results of a pilot clinical trial. World J Gastroenterol 15(8): 966-972.
BreathMatPlus (1997) Fully automated 13C-UBT mass spectrometer system for the diagnosis of gastric *Helicobacter pylori* infection. pp. 1-12.
Ciccocioppo (2003) Study of liver function in healthy elderly subjects using the 13C-methacetin breath test. Aliment Pharmacol Ther 17: 271-277.
Gasbarrini et al., (2004) Aminopyrine and methacetin 13C breath tests to assess hepatic function in HCV related chronic liver disease. Gastroenterology 126 (4): A743.
Fierbinteanu-Braticevici et al., (2013) The role of $^{13}$C-methacetin breath test for the non-invasive evaluation of nonalcoholic fatty liver disease. J Gastrointestin Liver Dis 22(2): 149-56.
Lingenfelser et al., (1998) Intravenous (13C)-methacetin breath test for evaluation of liver function in cirrhotic patients and healthy controls. Gastroenterology L0383.
Shirin et al., (2001) Evaluation of a novel continuous real time 13C urea breath analyser for *Heliobacter pylori*. Aliment Pharmacol Ther 15: 389-394.
United States Pharmacopeia 28, Acetaminophen Oral Solution, 2005.
Zipprich et al., (2003) 13C-methacetin metabolism in patients with cirrhosis: relation to disease severity, haemoglobin content and oxygen supply. Aliment Pharmacol Ther 17: 1559-1562.
Lock et al., (2009) Interpretation of non-invasive breath tests using (13)C-labeled substrates—a preliminary report with (13)C-methacetin. Eur J Med Res 14: 547-50.
Portincasa et al., (2006) Liver breath tests non-invasively predict higher stages of non-alcoholic steatohepatitis. Clin Sci (Lond) 111(2): 135-43.
Baruque et al., (2000) 13C-phenylalanine and 13C-methacetin breath test to evaluate functional capacity of hepatocyte in chronic liver disease. Dig Liver Dis 32(3): 226-32.
Stockmann et al., (2009) Prediction of postoperative outcome after hepatectomy with a new bedside test for maximal liver function capacity. Ann Surg 250(1): 119-25.

* cited by examiner

BREATH TEST DEVICE AND METHOD

BACKGROUND

The foregoing examples of the related art and limitations related therewith are intended to be illustrative and not exclusive. Other limitations of the related art will become apparent to those of skill in the art upon a reading of the specification and a study of the figures.

Liver disease has become one of the most common chronic illnesses, affecting tens of millions of people in the developed world, resulting in lifetime suffering and huge costs to the medical system. Viral hepatitis C (HCV) is one of the leading known causes of liver disease in the United States. It is a common cause of cirrhosis and hepatocellular carcinoma (HCC) as well as the most common reason for liver transplantation. At least 4 million people in United States are believed to have been infected with HCV, making HCV the most common chronic blood-borne infection nationally. Treatment for HCV has been successful in up to 60% of the cases, depending upon factors such as genotype, ethnicity, co-infections and other risk factors. In addition to the well-known chronic liver diseases due to viral hepatitis C(HCV), there is an increasing population with chronic liver diseases due to alcohol, autoimmune diseases, obesity and diabetes type 2 (associated with metabolic syndrome). Nonalcoholic fatty liver disease (NAFLD) has become a common chronic liver condition due to obesity and diabetes mellitus, affecting almost a quarter of the general population in the United States. The trend of rise in obesity in the western world is increasing annually. NAFLD includes a spectrum of liver conditions, ranging from simple steatosis (fat accumulation), also referred to as nonalcoholic fatty liver (NAFL), to nonalcoholic steatohepatitis (NASH) disease, which is associated with liver injury. NASH may progress from fibrosis to cirrhosis, as a consequence of the distortion of the normal liver architecture that interferes with blood flow through the liver. Cirrhosis can also lead to an inability of the liver to perform its biochemical functions, resulting in complications that cause liver failure and liver cancer. Then, transplantation would be the only feasible solution, and in many cases, even transplantation is not an option. Currently, there are several treatments in the pipeline for NASH, but there is no known approved and effective treatment currently available.

Breath tests that are based on monitoring the $^{13}CO_2$, which is a by-product of metabolization by the liver of $^{13}C$ labeled substrates, have been proposed as a tool for evaluation of liver function. Previously available tests for liver diseases generally involve drastically invasive procedures, and are therefore much less patient compliance than simple breath tests. Such procedures include biopsies of organs suspected of malfunction, blood tests and imaging technologies. It may take many years, if at all, until liver biopsy will be fully replaced. Although a biopsy is considered to yield reliable results, it is not the optimal tool for patient management since it is highly invasive, expensive, it requires day or overnight hospitalization of the patient and is very sensitive to sampling and analysis errors.

Blood tests for the detection of antibodies to suspected bacteria/virus and blood biochemistry tests include standard serum tests and tests following ingestion of suitable compounds. In any event, the blood tests do not specifically diagnose and distinguish NAFLD and NASH from other liver diseases. Most notably, the new serum tests (such as but not limited to FibroTest™) aim at correlation to fibrosis but have difficulties in detecting small changes in liver condition, which are needed for a genuine follow up. None of them have been adapted for use in routine clinical practice yet. They also suffer from the disadvantages of being performed at a central lab, thereby eliminating the economic benefit from the clinic.

Current imaging technologies, including ultrasound, Computed Tomography (CT), X-ray and Magnetic Resonance Imaging (MRI) cannot distinguish NAFLD from NASH. The new Fibroscan (ultrasound) test is not as effective with obese patients (a very significant (and growing) sector of the population) nor does it provide data on inflammation in the liver, nor does it provide information on actual liver function. Most imaging solutions (besides simple ultrasound which is useless for detecting fibrosis) do not exist at the standard medical clinic and thus such solutions necessitate the patients to leave the physician's clinic, which has its drawbacks, such as location, long waiting period, lack of economic benefits and more. A basic test in any of these devices (CT, X-ray and MRI) is expensive to highly expensive. Furthermore, there are other disadvantages to the previously used tests, such as the fact that they rarely give real time information about the organ function or status being observed. In some cases, such as in the case of blood tests for antibodies of bacterial infections, they give historic results which may have no current therapeutic relevance, since antibodies to a particular bacterium can remain in the body for up to 2 years from the date that the infection has been eradicated.

Moreover, the liver is an organ that has a very high metabolic capacity reserve. It is well known that a small part of a standard liver mass is sufficient to accomplish its physiological tasks. This poses a challenge when the liver has to be evaluated. Ideally the physician would like to get a quantitative evaluation of the liver mass, percentage of the cells that are functioning normally, or any other related parameter.

Furthermore, it is well known that the liver performs many tasks and thereby it is difficult to assess all of its functions with a single test. Furthermore, there are many factors that result in high intra and inter patient variability. Finally, different disease etiologies may impact different functions of the liver.

The use of two breath tests has been proposed to provide a more accurate picture of the liver diseases. It has been demonstrated that accuracy of evaluation can be improved by using more than one substrate.

Methacetin, also known as N-(4-Methoxyphenyl)acetamide, p-Acetanisidine, p-Acetanisidine and [N-(4-methoxyphenyl)ethanamide] is a compound having the formula:

Methacetin may be utilized for the evaluation of liver functional capacity and/or the extent of liver injury of "liver health". The biochemical basis for the evaluation of functional capacity is that the compound is metabolized by a cytochrome p450 enzyme expressed in normal liver cells (hepatocytes). Diseases of the liver that cause a loss in functional mass and/or impact the metabolic function of hepatocytes are associated with and may be correlated to a loss of capacity to metabolize methacetin.

One of the most common methods for determining the rate of metabolism of methacetin is to analyze the rate of metabolism of the methoxy group ($CH_3O$) of methacetin to carbon dioxide, which is excreted in exhaled breath. To distinguish the carbon dioxide derived from methacetin from all other sources of carbon dioxide, the methoxy group is labeled with $^{13}C$, a stable isotope of carbon. Thus all the $CO_2$ derived from methacetin will contain $^{13}C$ ($^{13}CO_2$) in contrast to all other sources of $CO_2$, which will contain approximately 99% $^{12}C$, and 1% $^{13}C$, the naturally abundant isotope. Thus, the rate of excretion of $^{13}CO_2$ (normalized to $^{12}CO2$) above background following the administration of methacetin-methoxy-$^{13}C$ indicates its rate of metabolism, which relates to the hepatic cell "health" and to the functional mass of the liver.

In common tests 75 mg of methacetin-methoxy$^{13}C$ is dissolved in 50-200 ml of water and taken orally following which the excretion rate of $^{13}CO2$ in exhaled air (breath testing {BT}) is determined at intervals of 15 minutes up to 2 hr. It has been reported that individuals with well-established cirrhosis have a statistically significant reduction in the rate of metabolism of methacetin but considerable overlap exists between a group of volunteers having normal liver function and those with milder stages of potentially progressive liver disease and/or the degree of liver injury.

The probable causes for the wide variation in the methacetin breath testing within the normal population, which makes it difficult to distinguish it from the population with mild loss of functional capacity, need to be addressed and overcome as well as the intra-patient test variability. There is a need for a modified test that would enhance the usefulness of the methacetin in breath test for evaluating liver functional capacity and/or hepatic injury or health.

Octanoic acid, a medium-chain fatty acid and salts thereof undergo a metabolic process in the mitochondria of the liver cells. These compounds may be used in the assessment of hepatic mitochondrial β-oxidation. There is a need in the art for a test that would allow accurate evaluation of hepatic related conditions.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other advantages or improvements.

According to some embodiments, there are provided breath test devices and methods that may be used for the evaluation of liver functional and metabolic capacity or to assess liver heath and/or degree of liver injury.

In one embodiment, there is provided a method of evaluating a liver condition, the method includes measuring a change in isotope ratio of a metabolic product of methacetin, or a salt or a derivative of methacetin, in a subject's breath following administration of an isotope labeled methacetin, or a salt or a derivative thereof in a water solution, wherein the methacetin, or a salt or a derivative thereof is substantially dissolved in the solution.

In another embodiment, there is provided a method of evaluating a liver condition, the method includes on-line monitoring a metabolic product of methacetin, a salt or a derivative of methacetin, in a subject's breath after administering to the subject isotope labeled methacetin, a salt or a derivative thereof in water solution form. The method may further include monitoring $CO_2$ in breath. The method may further include analyzing at least one breath related parameter obtained by monitoring the metabolic product of methacetin in combination with at least one breath related parameter obtained by monitoring $CO_2$ in breath.

In yet another embodiment, there is provided a method of measuring the peak height and/or time of appearance of the peak and/or combination thereof, of a metabolic product of methacetin, a salt or a derivative of methacetin, in a subject's breath after administering to the subject isotope labeled methacetin, a salt or a derivative thereof.

In yet another embodiment, there is the method measuring the slope of rate of metabolization of methacetin, a salt or a derivative of methacetin, in a subject's breath after administering to the subject isotope labeled methacetin, a salt or a derivative thereof.

In yet another embodiment, there is provided a method of evaluating a liver condition, the method includes on-line monitoring a metabolic product of octanoic acid, a salt or a derivative of octanoic acid, in a subject's breath after administering to the subject isotope labeled octanoic acid, a salt or a derivative thereof.

In yet another embodiment, there is provided a method of measuring the peak height and/or time of appearance of the peak and/or combination thereof, of a metabolic product of octanoic acid, a salt or a derivative of octanoic acid, in a subject's breath after administering to the subject isotope labeled octanoic acid, a salt or a derivative thereof.

In yet another embodiment, there is the method measuring the slope of rate of metabolization of octanoic acid, a salt or a derivative of octanoic acid, in a subject's breath after administering to the subject isotope labeled octanoic acid, a salt or a derivative thereof.

In another embodiment, there is provided a method of distinguishing between diagnosis of non-alcoholic steatohepatitis and nonalcoholic fatty liver, the method includes monitoring a metabolic product of octanoic acid, a salt or a derivative of octanoic acid, in a subject's breath after administering to the subject isotope labeled octanoic acid, a salt or a derivative thereof, wherein the method is based on the higher degree of metabolization in a subject having nonalcoholic fatty liver in comparison with a subject having non-alcoholic steatohepatitis and with a subject exhibiting normal liver function.

In another embodiment, there is provided a method of evaluating a liver condition, the method includes continuously monitoring a metabolic product of octanoic acid, a salt or a derivative of octanoic acid, in a subject's breath after administering to the subject isotope labeled octanoic acid, a salt or a derivative thereof.

In another embodiment, there is provided a device for evaluating a liver condition, the device includes one or more sensors adapted to monitor on-line an isotope level of a metabolic product of labeled methacetin, or a salt or a derivative of methacetin in a subject's breath and a controller adapted to sample measurements of the one or more sensors at a continuous mode.

In another embodiment, there is provided a device for evaluating a liver condition, the device includes one or more breath sensors adapted to monitor an isotope level within a metabolic product of labeled octanoic acid, or a salt or a derivative of octanoic acid and a controller adapted to on-line sample measurements of the one or more sensors at a continuous mode.

In another embodiment, there is provided a kit for use in the evaluation of a liver condition, the kit includes isotope labeled methacetin, or a salt or a derivative thereof and water at least the amount sufficient to substantially dissolve the isotope labeled methacetin, or a salt or a derivative thereof, wherein the isotope labeled methacetin, or a salt or a derivative thereof and the water are not in direct contact with each other.

In another embodiment, there is provided a kit for use in the evaluation of a liver condition, the kit includes isotope labeled methacetin, or a salt or a derivative thereof in a water solution, wherein the labeled methacetin, or a salt or a derivative thereof is substantially dissolved in the water.

BRIEF DESCRIPTION OF THE DRAWINGS

Exemplary embodiments are illustrated in the referenced figures and drawings. It is intended that the embodiments and figures disclosed herein are to be considered illustrative rather than restrictive.

DETAILED DESCRIPTION

While a number of exemplary aspects and embodiments have been discussed above, those of skill in the art will recognize certain modifications, permutations, additions and sub-combinations thereof. It is therefore intended that the following appended claims and claims thereafter introduced be interpreted to include all such modifications, permutations, additions and sub-combinations as are within their true spirit and scope.

In the following description, various aspects of the invention will be described. For the purpose of explanation, specific configurations and details are set forth in order to provide a thorough understanding of the invention. However, it will also be apparent to one skilled in the art that the invention may be practiced without specific details being presented herein. Furthermore, well-known features may be omitted or simplified in order not to obscure the invention.

In one embodiment, there is provided a method of evaluating a liver condition, the method includes measuring a change in isotope ratio of a metabolic product of methacetin, or a salt or a derivative of methacetin, in a subject's breath following administration of an isotope labeled methacetin, or a salt or a derivative thereof in a water solution, wherein the methacetin, or a salt or a derivative thereof is substantially dissolved in the solution.

The term "substantially dissolved" may include over 90% of methacetin, a salt or a derivative of methacetin dissolved in the solution. The term "substantially dissolved" may include over 99% of methacetin, a salt or a derivative of methacetin dissolved in the solution. The methacetin used herein may be any pre-made and/or pre-prepared solution of methacetin in a solvent, such as sterile or filtered water, with or without preservatives.

In another embodiment, there is provided a method of evaluating a liver condition, the method includes on-line monitoring a metabolic product of methacetin, a salt or a derivative of methacetin, in a subject's breath after administering to the subject isotope labeled methacetin, a salt or a derivative thereof in water solution form. The subject may exhibit normal enzymatic (for example, liver related enzymes) activity. The method may further include monitoring $CO_2$ in breath. The method may further include analyzing at least one breath related parameter obtained by monitoring the metabolic product of methacetin in combination with at least one breath related parameter obtained by monitoring $CO_2$ in breath. The method may further include analyzing at least one breath related parameter obtained by monitoring the metabolic product of methacetin in combination with at least one physiological and/or medical parameter. The physiological and/or medical parameter may include age, gender, weight, height, blood related parameters, body mass index (BMI), waist circumference, medication therapy related parameter or any combination thereof.

The method may further include the follow-up of liver condition, wherein the method may further include repeating, after a predetermined period of time, the step of on-line monitoring a metabolic product of methacetin, a salt or a derivative of methacetin, in a subject's breath after administering to the subject isotope labeled methacetin, a salt or a derivative thereof.

In yet another embodiment, there is provided a method of measuring the peak height and/or time of appearance of the peak and/or combination thereof, of a metabolic product of methacetin, a salt or a derivative of methacetin, in a subject's breath after administering to the subject isotope labeled methacetin, a salt or a derivative thereof.

Figure 1:
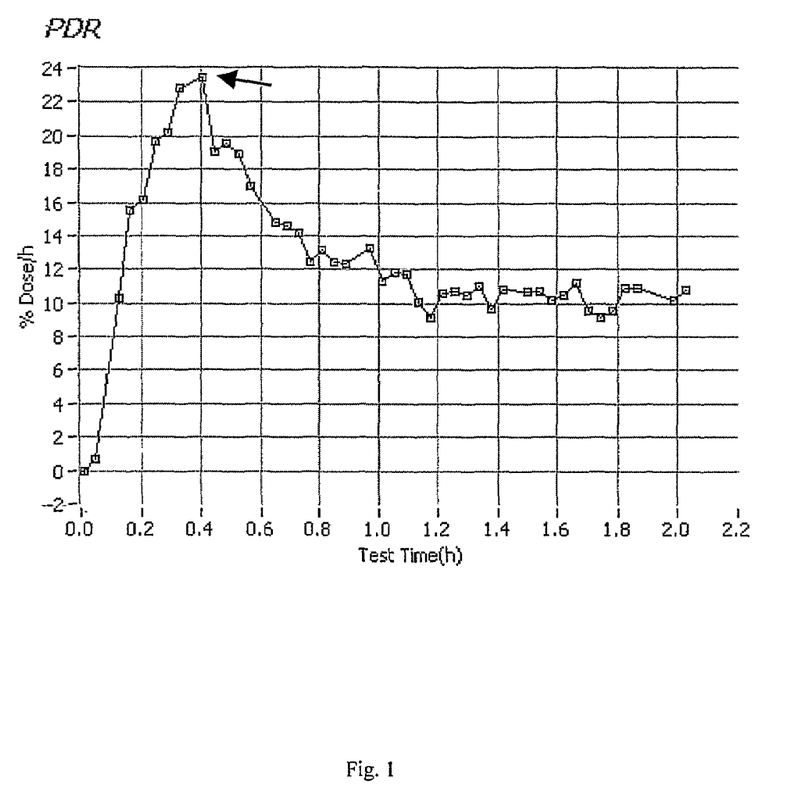
FIG. 1 shows a $^{13}$C-Methacetin Breath Test PDR (Percentage Dose Recovery) Curve, according to some embodiments.

Reference is now made to FIG. 1, which shows a $^{13}$C-Methacetin Breath Test PDR (Percentage Dose Recovery) Curve, according to some embodiments. The curve depicts the rate of metabolism of $^{13}$C-Methacetin in % dose/hour as measured in breath. The peak of the curve (marked by the arrow) appears after 0.4 h (hours). The PDR peak height is approximately at 23.5% dose/hour.

In yet another embodiment, there is provided a method of evaluating a liver condition, the method includes measuring the slope of rate of metabolization, known in the art as percent dose recovery (PDR), of methacetin, a salt or a derivative of methacetin, in a subject's breath after administering to the subject isotope labeled methacetin, a salt or a derivative thereof.

In yet another embodiment, there is provided a method of evaluating a liver condition, the method includes on-line monitoring a metabolic product of octanoic acid, a salt or a derivative of octanoic acid (such as, but not limited to, octanoate), in a subject's breath after administering to the subject isotope labeled octanoic acid, a salt or a derivative thereof.

In another embodiment, there is provided a method of distinguishing between diagnosis of non-alcoholic steatohepatitis and nonalcoholic fatty liver, the method includes monitoring a metabolic product of octanoic acid, a salt or a derivative of octanoic acid, in a subject's breath after administering to the subject isotope labeled octanoic acid, a salt or a derivative thereof, wherein the method is based on the higher degree of the metabolization in a subject having non-alcoholic fatty liver in comparison with a subject having non-alcoholic steatohepatitis and with a subject exhibiting normal liver function.

In another embodiment, there is provided a method of evaluating a liver condition, the method includes continuously monitoring a metabolic product of octanoic acid, a salt or a derivative of octanoic acid, in a subject's breath after administering to the subject isotope labeled octanoic acid, a salt or a derivative thereof. The method may be used in distinguishing between a nonalcoholic fatty liver and non-alcoholic steatohepatitis conditions in a subject. The method may further include monitoring $CO_2$ in breath. The method may further include analyzing at least one breath related parameter obtained by monitoring the metabolic product of octanoic acid in combination with at least one breath related parameter obtained by monitoring $CO_2$ in breath. The method may further include analyzing at least one breath related parameter obtained by monitoring the metabolic product of octanoic acid in combination with at least one physiological and/or medical parameter. The physiological and/or medical parameter may include age, gender, weight, height, blood related parameter, body mass index (BMI), waist circumference, medication therapy related parameter or any combination thereof. The device may further include a processor adapted to analyze at least one breath related parameter obtained by monitoring isotope level of a metabolic product of the labeled methacetin, or a salt or a derivative of methacetin in combination with at least one breath related parameter obtained by monitoring CO2 in breath.

In yet another embodiment, there is provided a method of measuring the peak height and/or time of appearance of the peak and/or combination thereof, of a metabolic product of octanoic acid, a salt or a derivative of octanoic acid, in a subject's breath after administering to the subject isotope labeled octanoic acid, a salt or a derivative thereof.

In yet another embodiment, there is the method measuring the slope of rate of metabolization of octanoic acid, a salt or a derivative of octanoic acid, in a subject's breath after administering to the subject isotope labeled octanoic acid, a salt or a derivative thereof.

Figure 2:
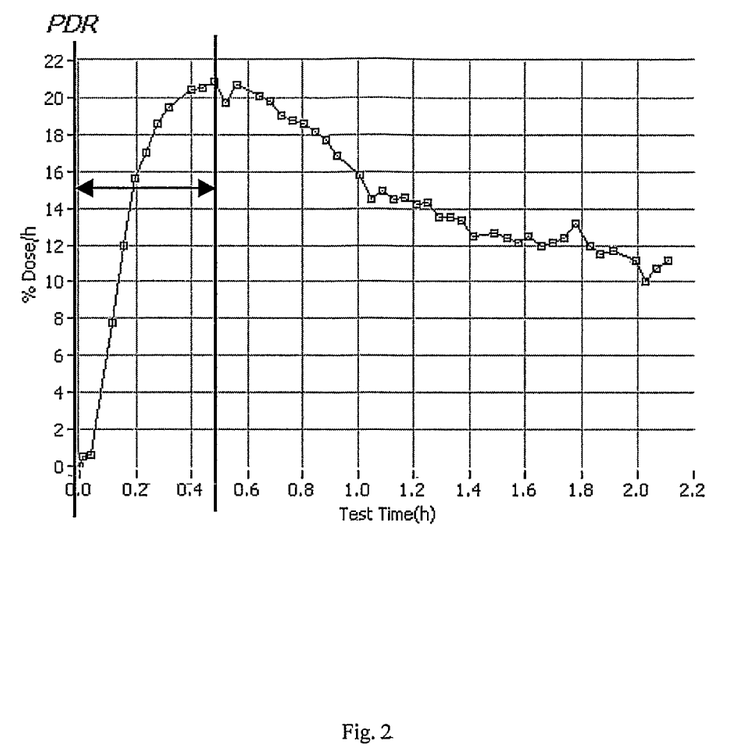
FIG. 2 shows a $^{13}$C-Octanoate Breath Test PDR (Percentage Dose Recovery) Curve, according to some embodiments.

Reference is now made to FIG. 2, which shows a $^{13}$C-Octanoate Breath Test PDR (Percentage Dose Recovery) Curve, according to some embodiments. The curve depicts the rate of metabolism of $^{13}$C-Octanoate in % dose/hour as measured in breath. The peak of the curve appears after 0.475 h (as shown by the arrow). The PDR peak height is approximately at 20.5% dose/hour.

Figure 3:
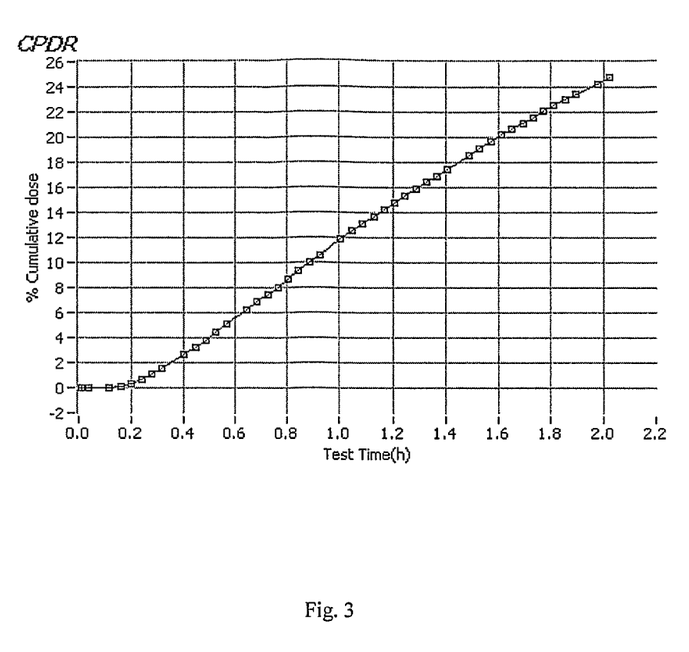
FIG. 3 shows a $^{13}$C-Methacetin/Octanoate Breath Test CPDR (Cumulative PDR) Curve, according to some embodiments.

FIG. 3 shows a $^{13}$C Octanoate Breath Test CPDR (Cumulative PDR) Curve, according to some embodiments. The curve depicts the total amount of labeled $^{13}$C Octanoate metabolized in %, as measured in breath. Similar curves may be produced by measuring other substances, such as $^{13}$C methacetin or any other appropriate substance.

According to some embodiments, a breath test method is provided for distinguishing between levels of fibrosis in various liver diseases (such as HCV, NASH), the method may include evaluating the liver function by monitoring a metabolic product of methacetin in a subject's exhaled breath and detection of increased or induced metabolization in early stages of fibrosis. The levels of fibrosis may include 0, 1 and 2 levels. The fibrosis may be related to a liver disease.

According to some embodiments, a breath test method for the follow-up of liver condition is provided, the method may include performing a first evaluation of the liver function by monitoring a metabolic product of methacetin in a subject's exhale and performing a second evaluation, after a predetermined period of time, of the liver function by monitoring a metabolic product of methacetin in a subject's exhale. In another embodiment, the step of performing a second evaluation, after a predetermined period of time, of the liver function by monitoring a metabolic product of methacetin in a subject's exhale may be repeated a multiplicity of times.

According to some embodiments, a breath test method for detecting subjects having a liver condition and a normal enzymatic activity, the method may include evaluating the liver function of a subject by monitoring a metabolic product of methacetin in the subject's exhale.

According to some embodiments, a breath test method for distinguishing between NASH and NAFL in a subject suffering from NAFLD and/or to distinguish between healthy controls and NAFL or NASH patients is provided, the method may include evaluating the liver function by monitoring a metabolic product of octanoic acid, a salt, an ester or a derivative thereof in a subject's exhale. In one embodiment, distinguishing between diagnosis of NASH and NAFL may be based on the increase of the liver function in a subject having NAFL in comparison to a subject having NASH and healthy subjects.

According to some embodiments, any breath test method for evaluating liver condition, liver function, metabolic capacity and/or to assess liver heath and/or degree of liver injury, provided herein may further include administering to the subject a test meal that may challenge the liver in a way that the "essentially all" liver has to function to a normal extent to metabolize the test meal rapidly and effectively.

According to some embodiments, any breath test method for evaluating liver condition, liver function, metabolic capacity and/or to assess liver heath and/or degree of liver injury provided herein may further include monitoring $CO_2$ in breath for example, by capnography. This may enable minimizing-test length and variations in metabolic rate and/or $CO_2$ production that would introduce non-relevant variables to liver test evaluation.

In another embodiment, the disclosure relates to a method for the evaluating liver functional capacity and/or health. In another embodiment, the disclosure relates to a method for testing liver functional capacity. In another embodiment, the disclosure relates to a method for monitoring liver functional capacity. In another embodiment, the disclosure relates to a method for conducting a follow-up of liver functional capacity.

In another embodiment, a method is provided for evaluating liver functional capacity and/or health by analyzing breath test parameters that provide quantitative presentation of the dynamic of the liver response. In another embodiment, the incline slope following administration of substrate, the peak time, the peak height/peak time, and other appropriate parameters may be calculated and provided.

In another embodiment, there is provided a device for evaluating a liver condition, the device includes one or more sensors adapted to monitor on-line an isotope level of a metabolic product of labeled methacetin, or a salt or a derivative of methacetin in a subject's breath and a controller adapted to sample measurements of the one or more sensors at a continuous mode. The device may be used for distinguishing between levels of fibrosis.

In another embodiment, there is provided a device for evaluating a liver condition, the device includes one or more breath sensors adapted to monitor an isotope level within a metabolic product of labeled octanoic acid, or a salt or a derivative of octanoic acid and a controller adapted to on-line sample measurements of the one or more sensors at a continuous mode. The device may be used in distinguishing between a nonalcoholic fatty liver and non-alcoholic steatohepatitis conditions in a subject.

Any device disclosed herein may be adapted to sample measurements of the one or more sensors at a continuous mode, while the subject is coupled to the device during breath sampling. The term "coupled to the device" may include coupling through a nasal cannula. The device may be adapted to automatically collect and analyze breath samples.

Any device disclosed herein may further include one or more breath sensors, such as capnography sensors, adapted to monitor $CO_2$ in breath. The device may further include a processor adapted to analyze at least one breath related parameter obtained by monitoring isotope level within a metabolic product of a labeled substance, such as methacetin and/or octanoic acid, or any salt or derivative thereof, in combination with at least one breath related parameter obtained by monitoring $CO_2$ in breath. The processor may correct for changes in $CO_2$ exhaled/production of a subject throughout the breath test.

Any device disclosed herein may further include a processor adapted to analyze at least one breath related parameter obtained by monitoring the metabolic product of a substance, such as methacetin and/or octanoic acid or any salt or derivative thereof, in combination with at least one physiological and/or medical parameter. Physiological and/or medical parameter may include, for example, age, gender, weight, height, blood related parameter, body mass index (BMI), waist circumference, medication therapy related parameter, any combination thereof or any other relevant parameter.

According to some embodiments, there is provided an improved breath test analyzer which provides accurate results on-site in times of the order of minutes, and which may be capable of implementation as a low cost, low volume and weight, portable instrument. According to some embodiments, the device may be sufficiently sensitive to enable it to function on-line by continuously collecting and analyzing multiple samples of the patient's breath from the beginning of the test, and processing the outputs in real time, such that a definitive result is obtained within a short period of time, such as, but not limited to, in the order of a few minutes.

Such a breath test analyzer may be suitable for the detection of various disorders such as, but not limited to, metabolic, or organ malfunctions, and since it can provide results in real time without the need to send the sample away to a special testing center or central laboratory, can be used to provide diagnostic information to the patient in the context of a single visit to a physician's office, or at any other point of care in a health care facility.

In another embodiment, there is provided a kit for use in the evaluation of a liver condition, the kit includes isotope labeled methacetin, or a salt or a derivative thereof and water at least the amount sufficient to substantially dissolve the isotope labeled methacetin, or a salt or a derivative thereof, wherein the isotope labeled methacetin, or a salt or a derivative thereof and the water are not in direct contact with each other. The kit may further include means for combining the isotope labeled methacetin, or a salt or a derivative thereof and the water.

In another embodiment, there is provided a kit for use in the evaluation of a liver condition, the kit includes isotope labeled methacetin, or a salt or a derivative thereof in a water solution, wherein the labeled methacetin, or a salt or a derivative thereof is substantially dissolved in the water.

In one embodiment, a water-soluble form of methacetin a salt or a derivative thereof is provided. In another embodiment, the water-soluble form of methacetin may facilitate absorption of methacetin in comparison to non-treated methacetin. In another embodiment, the absorption of methacetin may be active or passive.

The term "form of methacetin" may be, according to some embodiments, a composition, complex, mixture, combination, compound, formulation, inclusion complex, and the like, that includes methacetin.

The term "water-soluble form of methacetin" may include, according to some embodiments, a form of methacetin having larger water solubility than methacetin alone.

In another embodiment, the disclosure also relates to pharmaceutical compositions, which may include a predetermined amount of water-soluble form of methacetin, a salt or a derivative thereof, together with one or more pharmaceutically acceptable carriers or excipients.

In one embodiment there is further provided a method for the preparation of a water-soluble form of methacetin a salt or a derivative thereof, the method may include dissolving a complexing agent in water and adding methacetin, a salt or a derivative thereof.

In another embodiment, the disclosure relates to use of the water-soluble form of methacetin, a salt or a derivative thereof for the preparation of a pharmaceutical composition for use in testing liver functional capacity and/or health.

According to some embodiments, detecting, monitoring, distinguishing; evaluating, measuring, differentiating, quantifying, and the like as referred to herein may be accomplished by any of the apparatuses, breath collection systems, analyzer units, calibration devices, algorithms and methods described herein, and/or, as exemplary embodiments, by any of the apparatuses, breath collection systems, analyzer units, calibration devices, algorithms and methods disclosed in U.S. Pat. No. 6,186,958, U.S. Pat. No. 6,491,643 and U.S. Pat. No. 6,656,127, US20030216660 and US20010021815.

More specifically, such devices, apparatuses and methods can be used for metabolic liver function test, which could be utilized to assess liver function. According to some embodiments, by administering a specific compound orally or intravenously, a compound is directly metabolized or removed by the liver from the blood and metabolized, and a metabolic product is then released into the blood and excreted in the bile, urine, saliva, or exhaled breath. Methods according to some embodiments may include measuring the amount of the administered product that remains in serum over time or the amount of metabolic product that is produced and/or the rate at which this product is excreted, provides a potentially accurate measure of hepatic metabolic function. Several compounds have been utilized to measure hepatic metabolic function in this manner including indocyanine green, galactose, aminopyrine, caffeine, lidocaine, phenylalanine and Methacetin [N-(4-Methoxy-phenyl)acetamide]. Previous studies of the hepatic metabolism of lidocaine to monoethylglycinexylodide (MEGX) have demonstrated that: a. declined metabolism was apparent with increasing liver fibrosis and with worsening stages of cirrhosis, b. improved metabolism was apparent with successful treatment of the underlying liver disease, and c. an accurate prediction of which patients with stable cirrhosis awaiting liver transplantation were at risk to develop future hepatic decompensation. The liver tests are aimed at the patient population with acute or chronic liver disease. This includes persons infected with hepatitis C, patients with NASH or alcoholic related liver disease, liver transplant patients and more. By the administration of a substrate that is exclusively (or almost exclusively) metabolized by the liver, at least during the breath testing procedure, liver function can be analyzed.

In accordance with one embodiment, there is provided a breath test analyzer, including a very sensitive gas analyzer, capable of measuring a ratio of two chemically identical gases with different molecular weights. The gas analyzer is capable of measuring small quantities of isotopically labeled gas, which may be present in the breath of a patient.

There are a number of different operational modes for each type of test for such a breath analyzer, in which the analysis is performed on-line in real time whilst a patient is continuing to provide breath for subsequent analyses. In a common mode of operation, a breath test analyzer senses exhaled breath of a patient before ingestion of an isotopically labeled substance, analyzes the exhaled breath of a patient for the percentage of isotopically labeled gas from the total exhaled gas of that composition, in order to obtain a baseline reading. At least one more similar analysis after ingestion of an isotopically labeled substance, provides an indication of a medical condition within a time period. The time period defined to be the last sensing, which is between the first sensing of the patient's exhaled breath and the second sensing. This feature differs these breath analyzers from all the rest, since it provide analyses in a very short time period.

In an alternative mode of operation, the analyses are made successively at times after ingestion of an isotopically labeled substance, and before the end of production of the isotopically labeled by-products of the substance, and the analyzer performs comparisons of the change from sample to sample of the percentage of the isotopically labeled gas in the total exhaled gas of that composition, and thereby provides an indication of a medical condition as soon as the detected change in gas composition percentage permits it, and before the end of production of the isotopically labeled by-products of the substance.

In accordance with some embodiments, there are at least two modes of analyzing the breath samples. The analyzer can either perform its analysis on individual exhaled breaths, or, as stated herein, it can perform its analysis on-line on multiple samples of the patient's breath, continuously collected from the patient. It is further described that the analyzer wherein the breaths of a patient are exhaled into a reservoir for collection, called a breath collection chamber, and later transferred by various methods to the sample measurement chamber. An advantage of the method described therein, is that the analyzer draws an averaged sample of breath for measurement, instead of individual breaths, thereby increasing accuracy. Another advantage is that it is possible to collect only the plateau parts of multiple breaths for analysis (the relevant portion of the exhale).

In accordance with a further embodiment, there is provided a breath test analyzer, which analyzes a first exhaled breath of a patient and a second exhaled breath of the patient for isotope labeled products generated in a patient's body after ingestion by the patient of an isotope labeled substance. By performing an analysis of a patient's first breath and second breath, at least the second breath being exhaled following patient's ingesting the substance, the analyzer provides an indication of a medical condition within a time period following the exhalation of the second breath, which is less than the difference in time between the exhalation of the first breath and the exhalation of the second breath.

In accordance with further embodiment, a breath test analyzer as described herein including a breath analysis chamber, a breath inlet conduit for conveying exhaled gas from a patient to the breath analysis chamber; and a gas analyzer operative to analyze gas in the breath analysis chamber and to conduct the first analyzing of gas exhaled by the patient's first breath and the second analyzing of the patient's second breath, at least the second breath being exhaled following ingestion by the patient of an isotope labeled substance.

Furthermore, for those embodiments which analyze samples collected from exhaled breaths of a patient, it is understood that the analyzer also incorporates a breath collection chamber, which may be a separate chamber, or part of the breath inlet conduit, or part of the breath analysis chamber. In the latter case, the analysis of the gas sample effectively takes place in the breath collection chamber.

In accordance with further embodiments, there is provided a breath test analyzer as described herein, and wherein the first breath of a patient is exhaled prior to ingestion of an isotopically labeled substance, and the second breath of a patient is exhaled following ingestion of the isotopically labeled substance.

In accordance with further embodiments, there is provided a breath test analyzer as described herein, and wherein both of the first and second breaths of a patient are exhaled following patient's ingestion of the isotopically labeled substance.

In accordance with further embodiments, a breath test analyzer that analyzes a breath of a patient for an isotope labeled products generated in the body of a patient after ingestion of an isotope labeled substance. The analyzer provides an indication of a medical condition existent in the patient, by analyzing at least two successive samples of the patient's breath, wherein the at least two successive samples of the patient's breath include at least one later sample exhaled following analysis of at least one earlier sample.

In accordance with further embodiment, a breath test analyzer as described herein and including a breath analysis chamber, a breath inlet conduit for conveying exhaled gas from a patient to the breath analysis chamber, and a gas analyzer operative to analyze gas in the breath analysis chamber and to conduct analyses of the at least two successive samples of the patient's breath, wherein the at least two successive samples of the patient's breath include at least one later sample exhaled following analysis of at least one earlier sample.

In accordance with another embodiment, there is provided a breath test analyzer which analyzes a patient's exhaled breath before and after a product of an isotope labeled substance ingested by the patient could be detected in the patient's breath, a first analysis of the patient's exhaled breath, which takes place prior to the product being detectable in the patient's breath and a second analyzing of the patient's exhaled breath taking place once the product could be detectable in the patient's breath. The analyzer provides an indication of a medical condition within a time period following the exhalation of the second breath, which is less than the difference in time between the exhalation of the first breath and the exhalation of the second breath.

There is further provided in accordance with other embodiments, a breath test analyzer which monitors on-line a first exhaled breath of a patient and a second or any of the following exhaled breath of the patient for the products of an isotope labeled substance ingested by the patient while the patient is coupled on-line to the device, or monitors the above mentioned exhaled breath and provides an indication of a medical condition while the patient is coupled to the device, or is continuously breathing into the device on-line. The patient whose breath is being analyzed may be on-line coupled to the device continuously from the monitoring of the first exhaled breath to the monitoring of the second or any of the following exhaled breath.

Further provided in accordance with embodiment, a breath test analyzer as described herein including of a breath analysis chamber, a breath inlet conduit for conveying exhaled gas from a patient to the breath analysis chamber, and a gas analyzer operative to analyze gas in the breath analysis chamber while the patient is on-line coupled to the device.

There is even further provided in accordance with another embodiment, a breath test analyzer as described herein and including a breath analysis chamber, a breath inlet conduit for conveying exhaled gas from a patient to the breath analysis chamber, and a gas analyzer operative to analyze gas in the breath analysis chamber and to provide an indication of a medical condition while the patient is coupled to the device.

There is also provided in accordance with another embodiment, a breath test analyzer as described herein and including a breath analysis chamber, a breath inlet conduit for conveying exhaled gas from a patient to the breath analysis chamber; and a gas analyzer operative to analyze gas in the breath analysis chamber and to provide an indication of a medical condition while the patient is breathing into the device.

In accordance with still another embodiment, there is provided a breath test analyzer as described herein and wherein the patient is coupled to a disposable breath input device.

In accordance with yet another embodiment, there is provided a medical sample analyzer which analyzes samples taken from a patient, and wherein either the taking or the analyzing of the samples is terminated automatically at a point in time determined by the results of the analyzing of the samples.

In accordance with even another embodiment, there is further provided a breath test analyzer which analyzes samples of a patient's breath for isotope labeled products generated in the patients body after ingestion by the patient of an isotope labeled substance, and wherein either the taking or the analyzing of the samples is terminated automatically at a point in time determined by the results of the analyzing of samples.

There is also provided in accordance with another embodiment, a medical sample analyzer as described herein, which analyzes samples taken from a patient and including a sample input port for receiving samples taken from the patient and an analyzing apparatus for analyzing the samples, and wherein the analyzing is terminated automatically at a point in time determined by the results of the analyzing of the samples.

There is further provided in accordance with another embodiment, a breath test analyzer as described herein and including a breath analysis chamber, a breath inlet conduit for conveying exhaled gas from a patient to the breath analysis chamber; and a gas analyzer operative to analyze gas in the breath analysis chamber and wherein the analyzing of samples from the patient is terminated automatically at a point in time determined by the results of the analyzing of the samples.

In accordance with another embodiment, there is further provided a breath test analyzer as described herein, and wherein the gas analyzer includes a gas discharge lamp, or an infra-red source which emits a discontinuous spectrum.

In accordance with another embodiment, there is provided a breath test analyzer as described herein, and wherein the results of the analyzing of successive samples are fitted to a curve, and an indication of a medical condition in a patient is determined by inspecting the derivative of the curve.

In accordance with another embodiment, there is further provided a method of breath testing which analyzes a first exhaled breath of a patient and a second exhaled breath of the patient for isotope labeled products generated in the patient's body after ingestion by the patient of an isotope labeled substance, and including the steps of performing a first analysis of the patient's first breath, subsequently performing a second analysis of the patient's second breath, at least the second breath being exhaled following the patient's ingesting the substance, and providing an indication of a medical condition within a time period following exhalation of the second breath which is less than the difference in time between exhalation of the first breath and exhalation of the second breath.

Further provided in accordance with another embodiment, a method of breath testing which analyzes a patient's exhaled breath for the product of an isotope labeled substance ingested by the patient, and including the steps of performing a first analyzing of the patient's exhaled breath prior to the product being detectable in the patient's breath, performing a second analyzing of the patient's exhaled breath once the product is detectable in the patient's breath, and providing an indication of a medical condition within a time period following the exhalation of the second breath which is less than the difference in time between the exhalation of the first breath and the exhalation of the second breath.

Furthermore, whereas all of the above mentioned embodiments have been described for breath analyzers which analyze a first exhaled breath of a patient and a second exhaled breath of the patient, it is understood that the operation of these embodiments are equally valid for breath analyzer which analyze a first sample collected from at least a first exhaled breath of a patient, and a second sample collected from at least a second exhaled breath of a patient.

Further more, this breath test analyzer is also sufficiently small that it can easily be accommodated in the office of a physician and its cost is also sufficiently low that its use in such an environment can be economically justified.

A specific substance, compound and/or composition may be administered (for example, for the purpose of breath tests), orally, intravenously, nasally, transdermally, rectally, in eye drops, using an implemented device, or in any other appropriate form. However, it should be clear to one of skill in the art that any method of administering a substance into a subject, either known today or to be developed in the future, may be applicable to the present invention and is contemplated. The substance (for example, a compound) may be directly metabolized or removed by the liver, and a metabolic product is then released into the blood and excreted in the bile, urine, saliva, or exhaled breath. Measuring the amount of the administered product that remains in serum over time or the amount of metabolic product that is produced and/or the rate, at which this product is excreted, provides a potentially accurate measure of hepatic metabolic function.

According to some embodiments, breath tests may utilize $^{13}C$-labeled substrates providing a safe and non-invasive means for measuring hepatic metabolism. $^{13}C$ is a stable, non-radioactive isotope, which can be incorporated into a specific location within the molecule of a test substrate so that after metabolization by the liver into $^{13}CO_2$, it would be released. The $^{13}C$-compound may be administered orally, rapidly absorbed and metabolized by the liver, and then the $^{13}CO_2$ may be measured in exhaled breath within a predetermined period of time.

In one embodiment, the predetermined period of time, as referred to herein, may be 10-60 minutes. In another embodiment, the predetermined period of time may be 0.5-5 minutes. In another embodiment, the predetermined period of time may be 10-120 minutes. In another embodiment, the predetermined period of time may be 1-10 minutes. In another embodiment, the predetermined period of time may be 5-15 minutes. In another embodiment, the predetermined period of time may be 10-30 minutes. In another embodiment, the predetermined period of time may be 15-45 minutes. In another embodiment, the predetermined period of time may be 30-60 minutes. In another embodiment, the predetermined period of time may be 1-2 hours. In another embodiment, the predetermined period of time may be 1.5-3 hours.

In another embodiment, the predetermined period of time may be 3-4 hours.

In one embodiment, the predetermined period of time may vary between measurements. Hepatic metabolism of the compound may be assessed by measuring the ratio of $^{13}C/^{12}C$ in exhaled breath. According to some embodiments, detecting, differentiating and quantifying $^{13}C$ and $^{12}C$, in exhaled $CO_2$ may be accomplished by any of the apparatuses, breath collection systems, analyzer units and methods described herein, and/or, as exemplary embodiments, by any of the apparatuses, breath collection systems, analyzer units, calibration devices, algorithms and methods disclosed in U.S. Pat. No. 6,186,958, U.S. Pat. No. 6,491,643 and U.S. Pat. No. 6,656, 127, US20030216660 and US20010021815. According to some embodiments, portable office-based system may continuously sense and collect exhaled breath and analyzes $CO_2$ in on-line in real-time through a nasal cannula worn by the patient, and may enable evaluation of liver function in real time, thereby providing a follow-up method in clinical hepatology. According to some embodiments, such a test has been designed to provide a sensitivity and accuracy required for accurate detection of clinically relevant variations as small as $1/1000$ in the $^{13}CO_2/^{12}CO_2$ ratio.

Though carbon-13 is the most commonly used isotopic replacement atom in such breath tests, according to some embodiments, other atoms may be used instead of or in addition to carbon-13, including but not limited to, carbon-14, nitrogen-15 and oxygen-18 and others.

According to one embodiment, liver function or liver mass or liver health or liver injury evaluation may be performed by monitoring the P450 enzyme activity, or any other appropriate means. In another embodiment, liver disease severity and detoxification activity may be evaluated by means of the ingestion of $^{13}C$-labeled aminopyrine, methacetin, caffeine citrate or any other appropriate means (depending on the specific function being tested) and breath detection of an increased level of $^{13}CO_2$.

According to one embodiment, the quantification of functional liver mass by means of the ingestion of $^{13}C$-labeled galactose, and breath detection of an increased level of $^{13}CO_2$ may be performed.

Evaluation of the Methacetin breath test for quantifying liver function indicates that some of the intra and inter variability previously reported, which makes it difficult to distinguish the normal population from those with liver disease can be attributed to determinants that affect the rate of intestinal absorption and consequently the amount of methacetin that is taken up by the liver per unit time. In these instances, the maximum rate of production of $^{13}CO_2$ may be affected by rates of intestinal absorption and not only by the maximum rates of metabolism by the liver, thus yielding falsely low values in the normal population, this applies to the dynamic response as well.

According to some embodiments, measurement of hepatic mitochondrial activity may be evaluated by means of the ingestion of $^{13}C$-labeled octanoic acid, and breath detection of an increased level of $^{13}CO_2$.

According to some embodiments, hepatic mitochondrial function efficiency may be evaluated by means of the ingestion of $^{13}C$-labeled ketoisocaproic acid, and breath detection of an increased level of $^{13}CO_2$.

Diagnosis of Fibrosis Liver Disease

According to some embodiments, a breath test method is provided for distinguishing between levels of fibrosis, for example, 0, 1 and 2 levels of fibrosis liver disease (for example but not limited to, based on METAVIR, ISHAK or Knodell or Brunt fibrosis scores), the method may include evaluating the liver function by monitoring a metabolic product of methacetin in a subject's exhale. In another embodiment, a breath test method is provided for monitoring the level of fibrosis liver disease based on the increase of the liver function in subjects while fibrosis is progressing from level 0 to level 1, the method may include performing a first evaluation of the liver function by monitoring a metabolic product of methacetin in a subject's exhale and performing a second evaluation, after a predetermined period of time, of the liver function by monitoring a metabolic product of methacetin in a subject's exhale. In another embodiment, the step of performing a second evaluation, after a predetermined period of time, of the liver function by monitoring a metabolic product of methacetin in a subject's exhale may be repeated a multiplicity of times.

In one embodiment, the term "multiplicity" may refer to any number higher than 1. In another embodiment, the term "multiplicity" may refer to any number higher than 2. In another embodiment, the term "multiplicity" may refer to any number higher than 3.

In another embodiment, distinguishing between levels 0, 1 and 2 of fibrosis liver disease is based on the increase of the liver function in subjects having level 1 fibrosis in comparison to subjects having levels 0 and 2. In another embodiment, the subject may be suffering from a chronic hepatitis C, B or NAFL/NASH.

In another embodiment, distinguishing between levels 0, 1 and 2 of fibrosis liver disease is based on combination of data from methacetin and octanoic acid breath tests, or their derivatives.

In yet another embodiment, distinguishing between NAFL and NASH disease is based on combination of data from breath tests of methacetin and octanoic acid, or its derivatives, performed on the same patient on different days.

In yet another embodiment, distinguishing between NAFL and NASH disease is based on combination of data from breath tests of methacetin and octanoic acid, or its derivatives, performed on the same patient on different days and other medical information (such as, age, BMI).

Follow-Up of Liver Condition

According to some embodiments, a breath test method for the follow-up of liver condition is provided, the method may include performing a first evaluation of the liver function by monitoring a metabolic product of methacetin in a subject's exhale and performing a second evaluation, after a predetermined period of time, of the liver function by monitoring a metabolic product of methacetin in a subject's exhale. In another embodiment, the step of performing a second evaluation, after a predetermined period of time, of the liver function by monitoring a metabolic product of methacetin in a subject's exhale may be repeated a multiplicity of times. In another embodiment, the follow-up may include a follow-up of the progression of liver condition. In another embodiment, the follow-up may include follow-up of the deterioration of liver condition, for example, but not limited to subjects suffering from acute and/or chronic liver disease. In another embodiment, the follow-up may include a follow-up of the improvement of liver condition.

In another embodiment, the term "liver condition" may refer to any liver related disease, malfunction, injury, transplantation, abnormality, fat accumulation, increased metabolism, decreased metabolism and others.

Screening Subjects Having a Liver Condition

According to some embodiments, a breath test method for detecting subjects having a liver condition and a normal enzymatic activity, the method may include evaluating the liver function of a subject by monitoring a metabolic product of methacetin in the subject's exhale. In another embodiment, the method may further include performing a second evaluation, after a predetermined period of time, of the liver function by monitoring a metabolic product of methacetin in a subject's exhale. In another embodiment, the step of performing a second evaluation, after a predetermined period of time, of the liver function by monitoring a metabolic product of methacetin in a subject's exhale may be repeated a multiplicity of times. In another embodiment, normal enzymatic activity may include normal alanine aminotransferase values.

Diagnosis of NAFL Vs. NASH

Octanoic acid, a medium-chain fatty acid, and salts thereof are a reliable substrate to assess hepatic mitochondrial β-oxidation by means of a breath test. Hepatic mitochondrial beta-oxidation plays a role in the pathogenesis of NAFLD. Increased lipid peroxidation and/or hepatic cell injury and/or impairment in metabolic cycles can differentiate between NASH and NAFL and between these conditions and healthy liver. Therefore, there is potential solution for the need in the art for a test that would allow the differentiation between NASH and NAFL and those who are healthy, based on evaluation of hepatic mitochondrial beta-oxidation.

According to some embodiments, a breath test method for distinguishing between NASH and NAFL in a subject suffering from NAFLD is provided, the method may include evaluating the liver function/health by monitoring a metabolic product of octanoic acid, a salt, an ester or a derivative thereof in a subject's exhale. In one embodiment, distinguishing between diagnosis of NASH and NAFL may be based on the increase of the liver function or metabolization of octanoic acid or a derivative thereof in a subject having NAFL in comparison to a subject having NASH.

In another embodiment, NAFLD may be diagnosed prior to distinguishing between diagnosis of NASH and NAFL. In another embodiment, high probability of NAFLD may be indicated by ultrasonic means. In another embodiment, liver diseases other than NAFLD may be excluded prior to distinguishing between diagnosis of NASH and NAFL. In another embodiment, liver diseases other than NAFLD may be excluded prior to distinguishing between diagnosis of NASH and NAFL by a blood test. In another embodiment, the blood test may include a biochemical serum test. In another embodiment use of other characterizes of individual patients are combined with breath test data such as body mass index (BMI), specific blood parameters, blood pressure, waist circumference, age, gender, etc. to improve evaluation of liver health. In another embodiment NAFL and/or NASH can be differentiated from patients with healthy liver Challenging the Liver The liver is an organ that has a very high metabolic capacity reserve. It is well known that a small part of a standard liver mass is sufficient to accomplish its physiological tasks. Ideally the physician would like to get a quantitative evaluation of the liver mass, percentage of the cells that are functioning normally, or any other related parameters.

According to some embodiments, a breath test method is provided for evaluating liver function, the method may include monitoring a metabolic product of methacetin, after administering to the subject, an isotopically labeled substrate and an activation test that may challenge the liver in a way that the "essentially all" liver has to function to a normal extent to metabolize the activation test.

In another embodiment the term "activation" may refer to the use of any substance(s) that induce liver activity, for example but not limited to, sugar, alcohol and other substances.

According to some embodiments, a breath test method is provided for evaluating liver function, the method may include monitoring a metabolic product of substrate, after administering to the subject, a dose of over the minimum amount of substrate required for evaluating liver function, where the dose may challenge the liver in a way that the "essentially all" liver has to function to a normal extent to metabolize the activation test. In another embodiment, substrate may comprise of isotopically labeled substrate. In another embodiment, substrate may comprise of isotopically labeled substrate and non-isotopically labeled substrate. In another embodiment, the dose may be higher than 75 mg. In another embodiment, the dose may be higher than 85 mg. In another embodiment, the dose may be 75-100 mg. In another embodiment, the dose may be higher than 100 mg.

In one embodiment, the term "monitoring" may refer to conducting a multiplicity of measurements. In another embodiment, conducting a multiplicity of measurements may be performed to obtain the metabolism rate of a certain substrate.

In one embodiment, the term "essentially all" may refer to a larger percent of liver cells that could be evaluated after administering the substrate alone without the activation.

In another embodiment, the term "challenge" may refer to induce the activity of a larger amount of liver cells than would be induced without the activation. In another embodiment, the term "challenge" may refer to induce the activity of a larger amount of liver cells than would be induced given the minimum amount of isotopically labeled substrate required for evaluating liver function.

In another embodiment, the term "substrate" may refer to any material that undergoes metabolism in the liver. In another embodiment, the term "substrate" may refer to methacetin. In another embodiment, the term "substrate" may refer to a combination of materials, for example, but not limited to, methacetin and octanoic acid, salt, ester or derivative thereof.

In one embodiment, a method is provided for the assessment of beta-oxidation/mitochondrial function together with microsomal function on the same day wherein first substrate is administered and when its metabolic rate is evaluated, the second substrate is administered. This enables to evaluate how different liver diseases and/or metabolic conditions and/or fat impact the beta-oxidation/mitochondrial function of hepatic (liver) cells and to evaluate how these cells perform their physiological task; metabolize materials. The "On-line" continuous analysis may enable the performance of these procedures. A non-limiting example of administering one substrate after the other is disclosed in US2005020931.

In one embodiment, two substrates (or more) are labeled with different isotopes so that they may be evaluated in parallel (for example labeling $^{13}C$ and $^{14}C$).

In one embodiment, two substrates (or more) wherein at least one substrate may be measured by breath test and the other by other means such as but not limited to, a dye measured optically through the skin (for example, the indocyanine green test)

In one embodiment, two substrates (or more) labeled with the same isotopes may be measured by breath test so that their average metabolism may be evaluated.

In one embodiment, algorithms that may correct for the impact of the traces of a first substrate to metabolization of the second substrate are provided. In another embodiments the algorithms may be based on empirical and other models. Similarly, according to other embodiments, a method is provided to correct the impact of the second substrate on metabolization of the first substrate if both substrates are administered simultaneously.

Formulations of Methacetin

To assess the maximum capacity of the liver or a particular enzyme in the liver to metabolize a compound such as methacetin and the rate of its metabolization, the total amount should be fully delivered to the liver as quickly and as completely as possible. In terms of classical enzyme kinetics one should be at zero order kinetics and not first-order kinetics. In zero order kinetics the amount of test substance exceeds the maximum capacity of the enzyme to metabolize it and therefore the rate of product production is an accurate measure of the maximum functionally capacity of the enzyme.

Solubility of Methacetin and Methacetin-$^{13}$C:

Since the use of a stable isotope of carbon does not alter the general physical and chemical properties, all studies with Methacetin-$^{13}$C may also apply to methacetin (unlabeled) and vice versa. According to some embodiments, the term "methacetin" may refer to an isotopically labeled methacetin. According to some embodiments, the term "isotopically labeled methacetin" may refer to $^{13}$C labeled methacetin. According to some embodiments, the term "$^{13}$C labeled methacetin" may refer to methacetin-methoxy$^{13}$C. According to some embodiments, the term "methacetin" may refer to a combination of isotopically labeled and non-labeled methacetin.

The solubility of methacetin in water is limited and therefore dissolving methacetin in tap water room temperature is difficult even at concentrations of 75 mg to 150 ml. Furthermore, methacetin can form microcrystals and/or granule forms that further make its dissolution difficult. Common practice is to use 75 mg in 150-200 ml of tap water used for oral administration but in most cases it is difficult to assure 100% dissolution. How much may undergo decomposition in the acid environment of the stomach or may precipitate from solution is not known with certainty and may vary considerably.

Another variable is the length of time that both the insoluble and soluble methacetin enters the small intestines where absorption begins. The absorbed compound enters portal vein blood and is delivered to the liver for metabolism. The insoluble fraction must await solution in the intestinal and pancreatic fluids that enter the lumen before absorption occurs. Thus the phase of intestinal absorption is relatively long and delivery to the liver closer to first-order rather than zero order kinetics, which lessens the ability to distinguish low from normal enzyme levels in the liver and therefore loss of liver function. Also, it introduced an uncontrolled variable that affects the inter and intra patient variability (crucial in any case also when patients are in more advanced stages of disease). The correct dosage form may improve absorption.

In one embodiment, there is provided a water-soluble form of methacetin a salt or a derivative thereof. In another embodiment, the water-soluble form of methacetin may facilitate absorption of methacetin in comparison to non-treated methacetin. In another embodiment, the absorption of methacetin may be active or passive. In another embodiment, there is provided a water-soluble form of methacetin a salt or a derivative thereof adapted to be fully delivered to the liver. In another embodiment, there is provided a water-soluble form of methacetin a salt or a derivative thereof adapted to be fully delivered to the liver at a period of time shorter than the period of time needed for delivering into the liver non-treated methacetin. In another embodiment, the term "fully" refers to 70-100%. In another embodiment, the term "fully" refers to 80-100%. In another embodiment, the term "fully" refers to 90-100%.

The term "form of methacetin" may be, according to some embodiments, a composition, complex, mixture, combination, compound, formulation, inclusion complex, and the like, that includes methacetin.

The term "water-soluble form of methacetin" may include, according to some embodiments, a form of methacetin having larger water solubility than methacetin alone.

In another embodiment, the water-soluble form of methacetin may include methacetin in combination with carrier molecule(s).

In another embodiment, the water-soluble form of methacetin may include a complex of methacetin. In another embodiment, the water-soluble form of methacetin may include an inclusion complex.

The term "complex of methacetin", according to some embodiments, may refer to methacetin reversibly associated to a complexing agent via non-covalent chemical bonds.

The term "complex of methacetin", according to another embodiment, may refer to methacetin, a salt or a derivative thereof that may be included inside the three-dimensional net of a complexing agent.

The term "inclusion complex of methacetin", according to some embodiments, may refer to methacetin, a salt or a derivative thereof that may be included in the inner cavity of the a complexing agent.

The term "complexing agent", according to some embodiments, may refer to a substance that is reversibly associated with methacetin (for example, but not limited to, polymers, cyclodextrins and the like).

In one embodiment, the water-soluble form of methacetin may be able to achieve a substantially (over 70% (w/v)) concentration in water. In one embodiment, the water-soluble form of methacetin may be able to achieve a substantially over 80%-90% (w/v) concentration in water. In one embodiment, the water-soluble form of methacetin may be able to achieve a substantial (over 90% (w/v)) concentration in water. In one embodiment, the water-soluble form of methacetin may be able to achieve over 99% (w/v) concentration in water.

In one embodiment, the molar ratio of methacetin and the complexing agent may be 1 to between 1 and 3. In another embodiment, the molar ratio of methacetin and the complexing agent may be 1 to between 1 and 2. In another embodiment, the molar ratio of methacetin and the complexing agent may be 1 to approximately 1.5.

In another embodiment, the molar ratio of methacetin and hydroxypropyl-beta-cyclodextrin may be 1 to 1. In another embodiment, the molar ratio of methacetin and hydroxypropyl-beta-cyclodextrin may be 1 to 1.7. In another embodiment, the molar ratio of methacetin and hydroxypropyl-beta-cyclodextrin may be 1 to between 1 and 3. In another embodiment, the molar ratio of methacetin and hydroxypropyl-beta-cyclodextrin may be 1 to between 1 and 2. In another embodiment, the molar ratio of methacetin and hydroxypropyl-beta-cyclodextrin may be 1 to between 1.5 and 2.

In another embodiment, the complexing agent may include unsubstituted or substituted cyclodextrin. In another embodiment, the cyclodextrin may include beta-cyclodextrin.

In another embodiment, the substituted cyclodextrin may include alkylated, hydroxyalkylated cyclodextrin or a combination thereof. In another embodiment, the hydroxyalkylated cyclodextrin may include hydroxypropyl-beta-cyclodextrin, hydroxyethyl-beta-cyclodextrin methyl-beta-cyclodextrin, glucose-beta-cyclodextrin, or the like or any combination thereof. In another embodiment, the hydroxyalkylated cyclodextrin may include hydroxypropyl-beta-cyclodextrin. In another embodiment, the beta-cyclodextrin may include 2-hydroxypropyl-beta-cyclodextrin.

Cyclodextrins are cyclic oligosaccharides consisting of 6, 7, or 8 glucopyranose units, usually referred to as alpha, beta or gamma cyclodextrins, respectively. These naturally occurring compounds have relatively rigid doughnut-shaped structures, and may be used as natural complexing agents. The unique structures of these compounds owe their stability to intramolecular hydrogen bonding between the $C_2$- and $C_3$-hydroxyl groups of neighboring glucopyranose units. The molecule takes on the shape of a torus with the $C_2$- and $C_3$-hydroxyls located around the larger opening and the more reactive $C_6$-hydroxyl aligned around the smaller opening. The arrangement of $C_6$-hydroxyls opposite the hydrogen bonded $C_2$- and $C_3$-hydroxyls forces the oxygen bonds into close proximity within the cavity, leading to an electron rich, hydrophobic interior. The size of this hydrophobic cavity is a function of the number of glucopyranose units forming the cyclodextrin. The solubility of natural cyclodextrins is very poor and initially this prevented cyclodextrins from becoming effective complexing agents. Chemical substitutions at the 2, 3, and 6 hydroxyl sites would greatly increase solubility. The degree of chemical substitution, as well as, the nature of the groups used for substitution, determines the final maximum concentration of cyclodextrin in an aqueous medium. Cavity size is a major determinant as to which cyclodextrin is used in complexation. "Fit" is critical to achieving good incorporation of cyclodextrins. Six glucopyranose unit compounds or alpha-cyclodextrins have small cavities, which are not capable of accepting many molecules. Eight-glucopyranose unit compounds or gamma-cyclodextrins may, in some cases, have larger cavities than some molecules to be incorporated and cyclodextrin hydrophobic charges cannot effectively interact to facilitate complexation. Hydrophobic molecules may be incorporated into the cavity of cyclodextrins by displacing water. This reaction may be favored by the repulsion of the molecule by water. This effectively encapsulates the molecule of interest within the cyclodextrin, rendering the molecule water-soluble. When the water-soluble complex is diluted in a much larger volume of aqueous solvent, the process may be reversed, thereby releasing the molecule of interest into the solution (The Source. (1991). Water-Soluble Complexes, Part 1: Cyclodextrins—What are they? Vol. 7 No. 3. incorporated herein by reference).

According to some embodiments, 75 mg of methacetin may be solubilized in 5 ml of 10-60% cyclodextrin in water. In another embodiment, 15 mg of methacetin may be solubilized in 75 ml of 10-50% cyclodextrin in water. In another embodiment, 15 mg of methacetin may be solubilized in 75 ml of 20-50% cyclodextrin in water. In another embodiment, 15 mg of methacetin may be solubilized in 75 ml of 30-50% cyclodextrin in water. In another embodiment, 15 mg of methacetin may be solubilized in 75 ml of 35-45% cyclodextrin in water. In another embodiment, 75 mg of methacetin may be solubilized in 5 ml of approximately 45% cyclodextrin in water.

According to some embodiments, the molar ratio between methacetin and cyclodextrin may be 1 to between 1-3. In another embodiment, the molar ratio between methacetin and cyclodextrin may be to between 1-2. In another embodiment, the molar ratio between methacetin and cyclodextrin may be 1 to approximately 1.5.

According to some embodiments, the complexing agent as referred to herein may include a polymer. In another embodiment, the polymer may include polyvinylpyrrolidone, hydroxyalkylcellulose, polyethylene glycol, sodium lauryl sulfate, Tween-80 any derivative thereof or any combination thereof.

According to some embodiments, the ratio between methacetin and the polymer may not be critical and may depend on the desired final dose of methacetin. According to some embodiments, the complexes may include from 10% to 50% by weight of methacetin according to the total weight of the complex. According to other embodiments, the complexes may include from 10% to 20% by weight of methacetin according to the total weight of the complex. According to other embodiments, the complexes may include from 15% to 25% by weight of methacetin according to the total weight of the complex. According to other embodiments, the complexes may include from 20% to 30% by weight of methacetin according to the total weight of the complex. According to other embodiments, the complexes may include from 30% to 40% by weight of methacetin according to the total weight of the complex.

According to some embodiments, the water-soluble form of methacetin may include an organic solvent. In another embodiment, the organic solvent may be a non-toxic organic solvent. In another embodiment, the water-soluble form of methacetin may include methacetin pre-dissolved in an organic solvent.

According to some embodiments, the water-soluble form of methacetin may be in the form of a dry solid, particulates, powder, particles and the like. In another embodiment, water may be added prior to administration.

Stability of Methacetin and Methacetin-$^{13}$C:

According to some embodiments, the water-soluble forms of methacetin as described herein may stabilize the methacetin and may prevent the loss of the methoxy group or other evidence of decomposition.

According to some embodiments, methacetin-$^{13}$C may be stable in water and does not undergo loss of the methoxy group or other evidence of decomposition.

Although cyclodextrins as a class of compounds are known to be useful for the solubilization of other chemicals, the solubility of methacetin in hydroxypropyl beta cyclodextrin is not predictable and other cyclodextrins such as alpha and gamma cyclodextrin, also known for their general solubilization properties, were found less effective in solubilizing methacetin.

Unexpected results showed potential enhancement of stability of the molecule may be attributable, according to some embodiments, to the allylic structure of methacetin, which makes it susceptible to oxidation. Within the torus it appears that the light energies that favor oxidation (decomposition) are absorbed by the sugar molecules and therefore shield the methacetin.

In another embodiment, the disclosure also relates to pharmaceutical compositions, which may include a predetermined amount of water-soluble form of methacetin, a salt or a derivative thereof, together with one or more pharmaceutically acceptable carriers or excipients.

In another embodiment, the pharmaceutical composition may be in any form, including but not limited to a liquid, solution, gel, solid, particulates, powder, particles and the like.

Pharmaceutically acceptable excipients may include water, binders, diluents, disintegrating agents, stabilizing agents, preservatives, lubricants, fragrances, flavoring agents, sweeteners and other excipients known in the field of the pharmaceutical technology. Carriers and excipients may include hydroxypropylcellulose, lactose, microcrystalline cellulose, calcium carbonate, starch, colloidal silicone dioxide, sodium starch glycolate, talc, magnesium stearate, polyvinylpyrolidone, and other excipients known in the field of the pharmaceutical technology.

Optionally, according to some embodiments, the pharmaceutical compositions may be combination products including one or more active components in addition to methacetin.

Pharmaceutical compositions in a solid dosage forms, may be in accordance with some embodiments, tablets with immediate release of the methacetin, effervescent tablets or dispersion tablets and capsules.

The pharmaceutical compositions may be prepared by methods known in the field of the pharmaceutical technology.

In contrast to the current form of administration, specifically, methacetin in water, it is possible, according to some embodiments, to deliver all the pre-determined amount of methacetin as a small bolus that quickly clears the esophagus and enter the stomach where some dilution by gastric juice can occur. In another embodiment, dilution of the bolus does not cause precipitation of the methacetin and it will all be delivered more quickly to the intestines for absorption.

In one embodiment, because a complexing agent, for example hydroxypropyl beta cyclodextrin maintains the solubility of methacetin, a greater concentration may come in contact with the intestinal mucosa and more rapid absorption ensues.

Thus, the administration of water-soluble form of methacetin more closely approaches zero order kinetics and may be a more uniform, test for functional liver capacity.

In one embodiment there is further provided a method for the preparation of a water-soluble form of methacetin a salt or a derivative thereof, the method may include dissolving a complexing agent in water and adding methacetin, a salt or a derivative thereof. In another embodiment, the method further includes stirring the mixture at a temperature in the range from about 20° C. to 100° C. (for example, but not limited to, stirring the mixture at a temperature in the range from about 20° C. to 30° C., until the methacetin, a salt or a derivative thereof are inserted is dissolved into the complex). In another embodiment, a complexing agent is used and or inserted into the complex at temperatures in the range of 20-100° C.

In another embodiment, the method further includes drying in any appropriate manner. For example, but not limited to, lyophilization, spray-drying and any other suitable method.

In another embodiment, the method further includes encapsulating the water-soluble form of methacetin. According to some embodiments, the capsule may be swallowed and dissolves in gastric juice in the stomach and may quickly enter the intestines as a small bolus. In another version the capsule may be enteric-coated and may not be dissolved until after entering the intestines. Dissolution of the capsule delivers the methacetin immediately and in large concentration to the absorbing surface thus yielding high concentrations in the portal vein, which delivers the medication to the liver.

In another embodiment, the disclosure relates to use of the water-soluble form of methacetin, a salt or a derivative thereof for the preparation of a pharmaceutical composition for use in testing liver functional capacity.

In accordance with some embodiments, the water-soluble form of methacetin may be used in any of the methods referred to herein. In another embodiment, the water-soluble form of methacetin may be used in any test that evaluates the liver function. In another embodiment, the water-soluble form of methacetin may be used in any breath test that evaluates the liver function. According to some exemplary embodiments, the water-soluble form of methacetin may be used in any method that would be known to one of skill in the art for testing a liver function, for example, as disclosed in the following publications: B. Braden, d. Faust, u. Sarrazin, s. Zeuzem, c. F. Dietrich, w. F. Caspary & c. Sarrazin, $^{13}$C-methacetin breath test as liver function test in patients with chronic hepatitis C virus infection, Aliment Pharmacol Ther 2005; 21: 179-185 and Klatt S, Taut C, Mayer D, et al. Evaluation of the $^{13}$C-methacetin breath test for quantitative liver function testing, Z Gastroenterol 1997; 35: 609-14, which are herein incorporated by reference.

EXAMPLES

Methacetin Solutions

Two Weeks/Three Month Stability Results

1. Tested Materials 1-1. Methacetin, PPG-400 and tween-80, were supplied by sponsor.

1-2. Sodium lauryl sulfate-(SLS): Analytical grade for HPLC.

1-3. Water: HPLC grade after 0.2 µl filter.

1-4. Acetonitrile: HPLC grade.

1-5. Methanol: HPLC grade.

1-6. Methacetin in sterile water.

2. Formulations Preparation

In the first three items, formulations containing 75 mg methacetin/200 mL solvent were prepared:

2-1. Formulation-1: 76.04 mg methacetin; 62.94 mg SLS; water to final volume of 200 mL.

2-2. Formulation-2: 75.87 mg methacetin; 4 mL PPG-400; water to final volume of 200 mL.

2-3. Formulation-3: 76.66 mg methacetin; 4 mL tween-80; water to final volume of 200 mL.

In the fourth formulation, 75 mg methacetin/100 mL solvent was prepared:

2-4 Formulation-4: 75.01 mg methacetin; dissolved in 70° C. sterile water to final volume of 100 ml.

3. Storage Conditions

The first three formulated solutions were stored at room temperature protected from light. The fourth solution was stored in an incubator for 3 months at 40° C.

4. Sample Preparation Before Analysis.

On each testing interval, the formulated samples were analyzed according to the following method:

Method of Analysis:

| HPLC conditions: | |
|---|---|
| Column: | Inertsil ODS-2, 5µ. 250 × 4.6 mm, |
| Column temp: | 30° C. |
| Detector: | UV at 240 nm |
| Flow: | 0.9 mL/min |
| Injection volume: | 15 µL |
| Run time: | 9 min |
| Mobile phase: | 30:70 ACN:H$_2$O |
| Blank: | M.P. |

The samples were diluted to a concentration of about 37 ppm and analyzed against a standard solution at the same concentration. The standard was provided by the sponsor (Adrich 428264 batch: UI 2335). Purity of 100% was used in calculations.

5. Methacetin Standard Solution Preparation.

The methacetin sample that was used for the formulations was also used as a standard for the HPLC determination.

Stock solutions containing 37-38 mg/100 mL methanol were found to be stable at room temperature for at least one week. The stock solution was diluted ×10 in mobile phase solution before the HPLC analysis.

6. Assay of Methacetin in the Formulations

The assay was conducted according to Analyst SOP No. 05-001-03, and the HPLC method that was provided by the sponsor.

7. Results

The results as given in Table 1, show that in the first three formulations methacetin was found stable at room temperature for two weeks, and the fourth formulation was found to be stable for 3 months.

TABLE 1

Stability results - summary

| Formulation no. | Time zero Assay (μg/mL) | Appearance | One week Assay (μg/mL) | Appearance | Two weeks Assay (μg/mL) | Appearance | Max. % difference from time zero |
|---|---|---|---|---|---|---|---|
| For 1 (SLS) Mean | 383.0 382.9 382.9 | Clear, no color, no precipitation | 380.9 381.2 381.0 | Clear, no color, no precipitation | 383.6 383.5 383.6 | Clear, no color, no precipitation | 0.5 |
| For 2 (PPG) Mean | 371.1 370.9 371.0 | turbid, no color, no precipitation | 369.1 369.5 369.3 | turbid, no color, no precipitation | 370.8 370.3 370.5 | turbid, no color, no precipitation | 0.5 |
| For 3 (TWEEN) Mean | 372.7 372.1 372.4 | Clear, no color, no precipitation | 371.1 371.2 371.1 | Clear, no color, no precipitation | 376.6 375.5 376.1 | Clear, no color, no precipitation | 1 |

Reproducibility and Stability of Single Dose Preparation of Methacetin in Sterile Water.

Table 2 shows the reproducibility and stability of sample preparation $^{13}$C Methacetin, 75 mg/100 ml (Analyst Research Laboratories)

TABLE 2

Reproducibility and Stability of $^{13}$C Methacetin

| Analyst # | mg/mL | Sample volume (mL) | Mg/bottle |
|---|---|---|---|
| Reproducibility | | | |
| 9644-1 | 0.79 | 95.0 | 75.3 |
| 9644-2 | 0.77 | 98.0 | 75.4 |
| 9644-3 | 0.77 | 97.0 | 74.2 |
| 9644-4 | 0.75 | 98.5 | 73.9 |
| 9644-5 | 0.77 | 97.5 | 75.2 |
| 9644-6 | 0.76 | 96.5 | 73.3 |
| 9644-7 | 0.77 | 97.0 | 74.5 |
| 9644-8 | 0.76 | 99.5 | 75.6 |
| 9644-9 | 0.76 | 98.0 | 74.1 |
| 9644-10 | 0.76 | 100.5 | 76.3 |

TABLE 2-continued

Reproducibility and Stability of $^{13}$C Methacetin

| Analyst # | mg/mL | Sample volume (mL) | Mg/bottle |
|---|---|---|---|
| Mean | 0.77 | 97.8 | 74.8 |
| % RSD | 1.5 | 1.6 | 1.2 |
| Stability (3 months at 40° C.) | | | |
| 9644-1 | 0.79 | 95.0 | 74.2 |
| 9644-2 | 0.77 | 98.0 | 74.1 |
| Mean | | | 74.2 |

Stability of Methacetin in Cyclodextrin

1. Formulation Preparation

Formulation containing 175 mg methacetin in 5 ml Cyclodextrin was prepared.

2. Methacetin Standard Solution Preparation.

Aqueous solutions of Methacetin were prepared in the laboratory at concentrations of ~500 ppm in 4 replicates. Methacetin content was determined by Reverse Phase UV Detection HPLC method at the day of preparation. The samples were stored at room temperature for the required time period of the analysis and were analyzed against prepared standard solutions.

3. Results

The results as given in Table 3, show that methacetin in the new formulation was found to be stable at room temperature for five weeks.

TABLE 4

Five weeks stability results - summary

| Formulation Methacetin and Cyclodextrin | TIME ZERO Assay (mg/5 mL) | Appearance | THREE WEEKS Assay (mg/5 mL) | Appearance | FIVE WEEKS Assay (mg/5 mL) | Appearance | Max. % difference from time zero |
|---|---|---|---|---|---|---|---|
| Mean | 175.0 175.0 175.0 | Clear, no color, no precipitation | 175.0 177.7 176.35 | Clear, no color, no precipitation | 168.75 178.0 173.375 | Clear, no color, no precipitation | 3.6 |

Additional examples, according to some exemplary embodiments are disclosed in Appendices A, B and C.

The invention claimed is:

1. A method of quantitatively evaluating a liver function and/or a degree of liver injury in a subject, the method comprising:
providing solution samples of isotope-labeled methacetin or a salt or a derivative thereof wherein the solution samples are produced in a process comprising:
mixing, in a pre-determined amount of water, a pre-determined amount of isotope-labeled methacetin or the salt or the derivative thereof, to produce a solution;
analyzing the solution to measure an amount of the methacetin or the salt or the derivative thereof dissolved in the solution; and providing for administration solution samples wherein, according to the analysis of the solution, at least 90% of the pre-determined amount of methacetin, or the salt or the derivative thereof, is dissolved in the solution;

administering the analyzed solution sample to a subject in need thereof;

following the administering, measuring a change in isotope ratio of a metabolic product of the isotope-labeled methacetin, or the salt or the derivative thereof, in the subject's breath using a breath sensor adapted to monitor the metabolic product of the isotope-labeled methacetin or the salt or the derivative thereof; and quantitatively evaluating the liver function and/or the degree of liver injury based on the measured change in the isotope ratio.

2. The method of claim 1, wherein the at least 90% of the pre-determined amount of methacetin, or the salt or the derivative thereof comprises over 99% of the pre-determined amount of isotope-labeled methacetin, the salt or the derivative thereof.

3. The method of claim 1, wherein administration comprises oral, intravenous, an implemented device, or any combination thereof.

4. The method of claim 1, wherein the isotope-labeled methacetin, or the salt or the derivative thereof comprises methacetin or salt or derivative thereof labeled with carbon-13, carbon-14, oxygen-18 or any combination thereof.

5. The method of claim 1, further comprising administering to the subject a test meal.

6. The method of claim 1, further comprising:
on-line monitoring a metabolic product of the isotope-labeled methacetin, the salt or the derivative thereof, in the subject's breath after administering the analyzed solution to the subject.

7. The method of claim 6, further comprising monitoring $CO_2$ in breath.

8. The method of claim 7, further comprising analyzing at least one breath related parameter obtained by measuring the change in the isotope ratio of the metabolic product of the isotope-labeled methacetin, the salt or the derivative thereof, in combination with at least one breath related parameter obtained by monitoring $CO_2$ in breath.

9. The method of claim 8, further comprising analyzing at least one breath related parameter obtained by measuring the change in the isotope ratio of the metabolic product of the isotope-labeled methacetin, the salt or the derivative thereof, in combination with at least one physiological and/or medical parameter.

10. The method of claim 9, wherein the physiological and/or medical parameter comprises age, gender, weight, height, blood related parameter, body mass index (BMI), waist circumference, medication therapy related parameter or any combination thereof.

11. The method of claim 6, further comprising a follow-up of the liver function and/or the degree of liver injury, wherein the method further comprises:

repeating, after a predetermined period of time, the step of on-line monitoring a metabolic product of the isotope-labeled methacetin, the salt or the derivative thereof, in a subject's breath after administering the analyzed solution to said subject.

12. The method of claim 11, wherein the predetermined period of time comprises between 0.5 minutes and 4 hours.

13. The method of claim 11, wherein the predetermined period of time comprises between 4 hours and 12 months.

14. The method of claim 6, wherein the subject exhibits a normal enzymatic activity.

15. The method of claim 1, wherein the evaluation of the liver function and/or degree of injury of the liver comprises distinguishing between levels of fibrosis.

16. The method of claim 15, wherein the levels of fibrosis comprise a level 0, a level 1 and a level 2, which correlate to the subject's levels of liver disease according to a standard fibrosis score.

17. The method of claim 16, wherein the fibrosis is related to a liver disease.

18. The method of claim 1, further comprising administering to the subject a liver challenging test meal.

19. The method of claim 1, wherein:
mixing, in the pre-determined amount of water, the pre-determined amount of isotope-labeled methacetin or the salt or the derivative thereof comprises stirring the isotope-labeled methacetin, the salt or the derivative thereof in the pre-determined water at a temperature in the range of 20° C.-100° C., and measuring the change in isotope ratio in the subject's breath comprises detecting a peak and measuring a peak height and/or time of appearance of the peak and/or combination thereof, of a metabolic product of the isotope-labeled methacetin, the salt or the derivative of methacetin by using a breath sensor adapted to monitor the metabolic product of the isotope-labeled methacetin or the salt or the derivative thereof, in the subject's breath.

20. The method of claim 1, wherein the evaluation of the liver function and/or the degree of injury of the liver comprises distinguishing between levels milder than cirrhosis.

21. The method of claim 20, wherein the levels milder than cirrhosis comprise a healthy liver.

22. The method of claim 1, wherein the analyzing comprises an Ultra-Violet (UV) absorption test.

23. The method of claim 1, wherein the analyzing comprises a High Pressure Liquid Chromatography (HPLC) analysis.

24. A method for follow-up of a liver function and/or a degree of liver injury of a subject, comprising repeating the method of claim 1 at intervals of a predetermined period of time.

25. The method of claim 24, wherein said predetermined period of time is between 4 hours and 12 months.

* * * * *